(12) United States Patent
Ballier

(10) Patent No.: US 6,610,061 B2
(45) Date of Patent: Aug. 26, 2003

(54) FIXATION DEVICE

(76) Inventor: Roland Ballier, Jagerhofstrasse 2, D-78532 Tuttlingen (DE)

( * ) Notice: Subject to any disclaimer, the term of this patent is extended or adjusted under 35 U.S.C. 154(b) by 82 days.

(21) Appl. No.: 09/897,403

(22) Filed: Jul. 3, 2001

(65) Prior Publication Data

US 2001/0051806 A1 Dec. 13, 2001

Related U.S. Application Data

(63) Continuation of application No. 09/400,436, filed on Sep. 21, 1999, now Pat. No. 6,283,965, which is a continuation-in-part of application No. 09/011,924, filed on Jun. 8, 1998, now Pat. No. 6,030,387.

(30) Foreign Application Priority Data

Jun. 17, 1996 (DE) ..................................... 296 10 638 U

(51) Int. Cl.[7] ............................................... A61B 17/64
(52) U.S. Cl. ............................. 606/59; 606/54; 606/104
(58) Field of Search ............................. 606/53, 54, 56, 606/59, 72, 75, 96, 104

(56) References Cited

U.S. PATENT DOCUMENTS 5,312,403 A * 5/1994 Frigg ........................... 606/54
5,578,032 A * 11/1996 Lalonde ....................... 606/54

FOREIGN PATENT DOCUMENTS

DE 41 13 083 C2 * 10/1992
DE 94 02 291 * 2/1994

* cited by examiner

Primary Examiner—David O. Reip
(74) Attorney, Agent, or Firm—Kenyon & Kenyon

(57) ABSTRACT

The invention relates to a fixation device with clamping jaws and with rods connecting the clamping jaws, said rods being adjustable axially and angularly for positioning relative to the clamping jaws and clampable in the desired position, and with fixation and retaining pins that are receivable in a clampable fashion in the clamping jaws. According to the invention, a fixation pin applicator can be connected in a releasable fashion to the clamping jaws. A fixation pin can be brought into a desired position by means of the fixation pin applicator.

24 Claims, 10 Drawing Sheets

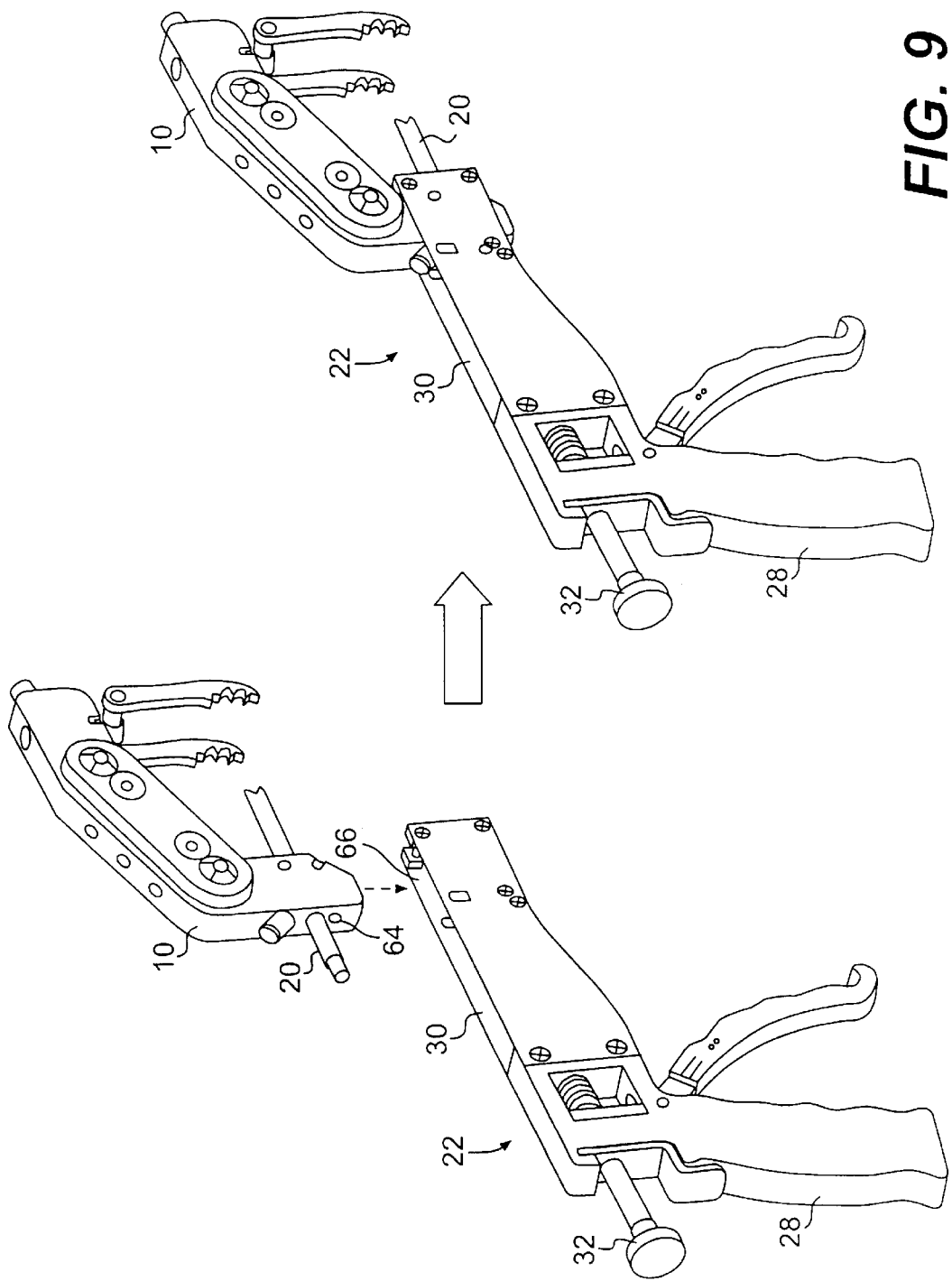

FIXATION DEVICE

RELATED APPLICATIONS

This is continuation of U.S. Ser. No. 09/400,436, filed on Sep. 21, 1999, now U.S. Pat. No. 6,283,965, which is a continuation-in-part of U.S. Ser. No. 09/011,924, filed on Jun. 8, 1998, now U.S. Pat. No. 6,030,387.

BACKGROUND OF THE INVENTION

The invention consists of a fixation device used to immobilize portions of a fractured bone relative to one another, and more specifically to a device to immobilize such portions of fractured bone by attaching an adjustable rigid frame to the fractured bone.

DESCRIPTION OF RELATED ART

A fixation device is known from DE 41 13 083 A1. This fixation device has three or four rings used as clamping jaws, said rings being designed as either closed or sector rings. The rings are connected with one another by rods. For mutual positioning of the rings, the rods are axially displaceable and pivotable with respect to the rings and can be clamped in position respective to the rings. Holders are provided on the rings for bone wires or bone fixation and retaining pins.

The known fixation device permits free relative movement of the rings in space, so that the bone fragments can be positioned and repositioned very exactly. The fixation device is secured in a stable fashion in precisely set positions by clamping the rods to the rings.

A fixation device is also known from DE 94 01 291 U, that has only two clamping jaws for provisional emergency care of the patient, with each sector ring having two holders for the clamping pins and with each holder having at least two receptacles for the clamping pins, i.e. the fixation and retaining pins. The receptacles are offset with respect to one another perpendicularly with respect to the plane of the sector ring. The clamping pins are designed as cylindrical pins that have a small point at their anterior ends, said point being capable of being pressed superficially into the bone. These clamping pins are provided with an external thread in their rear areas. After the clamping jaws are positioned, the clamping pins are then advanced by the suitably designed receptacle that cooperates with the external threads of the clamping pins until they rest on the surface of the bone and provide the necessary grip. This fixation of the clamping pins is cumbersome and time-consuming.

SUMMARY OF THE INVENTION

The present invention is directed to a fixation device that substantially obviates one or more of the problems due to limitations and disadvantages of the related art.

Additional features and advantages of the invention will be set forth in the description which follows, and in part will be apparent from the description, or may be learned by practice of the invention. The objectives and other advantages of the invention will be realized and attained by the apparatus and method particularly pointed out in the written description and claims hereof, as well as the appended drawings.

To achieve these and other advantages and in accordance with the purpose of the invention, as embodied and broadly described, the invention is a fixation device with clamping jaws having rods connecting the clamping jaws, said rods being adjustable axially and angularly relative to the clamping jaws and being clampable in a desired position, and with fixation and retaining pins that can be received in a clampable fashion in the clamping jaws. The device has a fixation pin applicator releasably connectable with the clamping jaws, by means of which applicator a fixation pin can be brought into a desired position.

Accordingly, the clamping jaws are releasably connectable with a fixation pin applicator, by means of which applicator a fixation pin can be brought into the corresponding desired position on the surface of the bone.

The fixation device offers a minimally invasive alternative to surgery of fractures of bones such as, for example, the tibia. The individual fragments are secured in the area of the cortex in each instance without the medullary cavity being opened (so-called pinless nail method). The fixation device can be applied rapidly and simply because of the fixation pin applicator provided according to the invention, and permits intra operative and postoperative repositioning of the device and of the bone fragments in all planes.

This technique avoids contamination of the medullary cavity. A direct procedural change to using the marrow nailing method poses no risk, i.e., it can be performed without an increased risk of infection. In addition, when the fixation device according to the invention is used, the device can remain in place even during marrow nailing, if that procedure is required, considerably simplifying marrow nailing and also allowing the procedure to be performed more rapidly.

In a different embodiment, the invention is a fixation device that includes a fixation pin applicator that can be designed in the form of a pistol, and can have in addition to a fixed handle, a movable handle part by which a plunger acting on the fixation pin can be displaced.

In the fixation pin applicator, a transport plate for moving the plunger against the force of a spring can be moved by the movable handle part. The plunger and therefore the fixation pin is thus moved toward the desired position by this transport plate.

The fixation pin applicator can be secured to the clamping jaw by a latching mechanism with a catching pin in an especially simple fashion. To release the latching mechanism, the fixation pin applicator has an externally operable release that is connected to the spring loaded latching mechanism. The clamping jaw can also be held in place by a spring loaded ball affixed to the fixation pin applicator, and cooperating with a corresponding depression in the clamping jaw.

The fixation device can consist of two clamping jaws that can be maintained in the desired position with respect to one another by corresponding rods. According to one advantageous embodiment of the invention, however, additional connecting elements can be linked to the clamping jaws, said elements having suitable clamping devices to receive additional rods and hence to connect additional clamping jaws. The fixation device can thus be expanded as desired.

The fixation and retaining pins can have different shapes. In particular, the retaining pins can be made straight or bent. They can also be designed as so-called dual pins, which are forked pins located parallel to one another. The retaining pins can also be made spoon-shaped at their ends and provided with a plurality of points parallel to one another. These pins also can be in the form of single or dual pins.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, are incorporated in and constitute a part of this specification, illustrate embodiments of the invention and, together with the description, serve to explain the objects, advantages, and principles of the invention.

In the drawings,

FIG. 9 is a diagram illustrating the connection process between the clamping jaw and the fixation pin applicator;

DETAILED DESCRIPTION OF THE EMBODIMENTS

Figure 1:
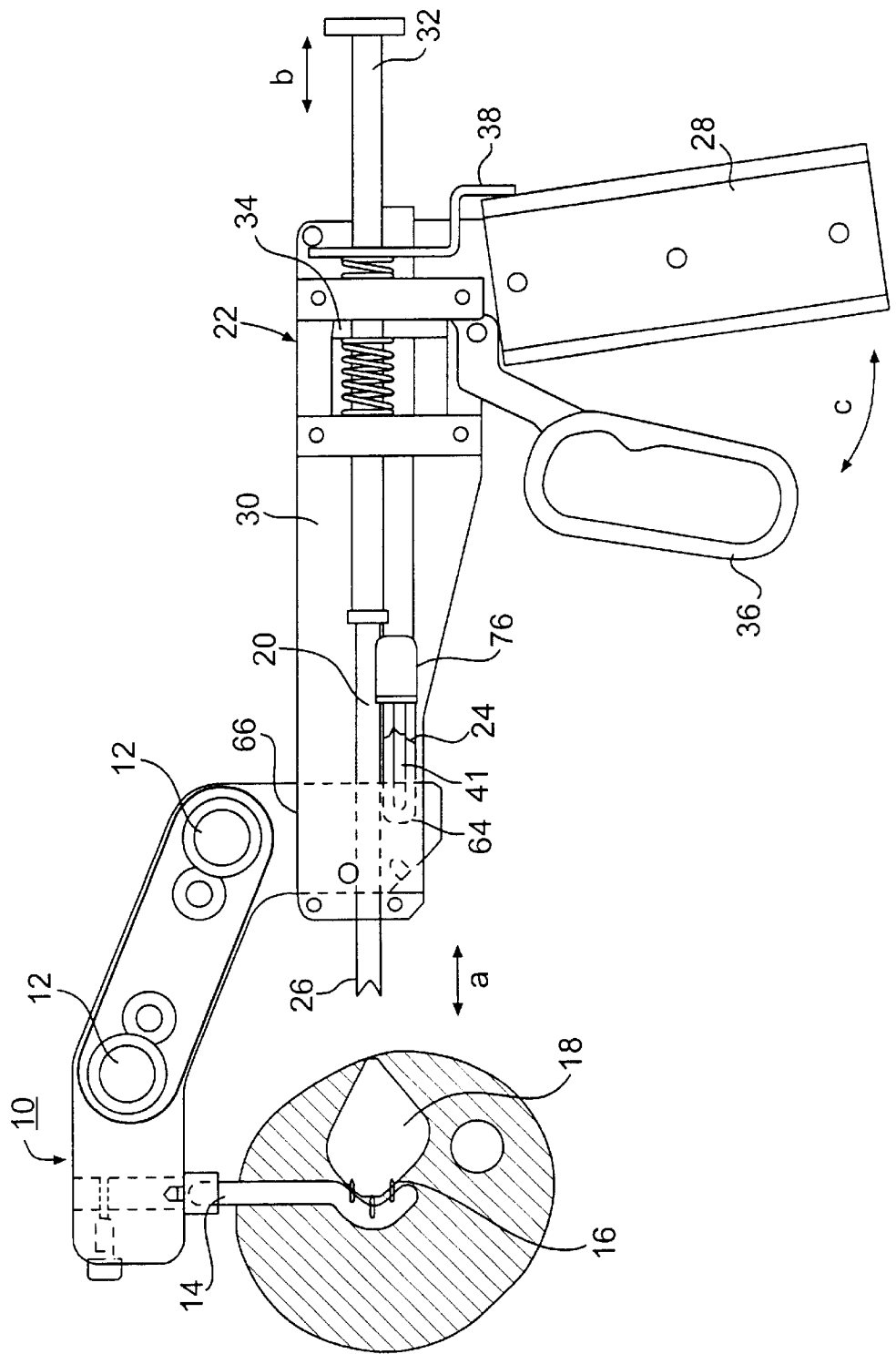
FIG. 1 is a side elevation view of the fixation device with the fixation pin applicator in place.
Figure 2:
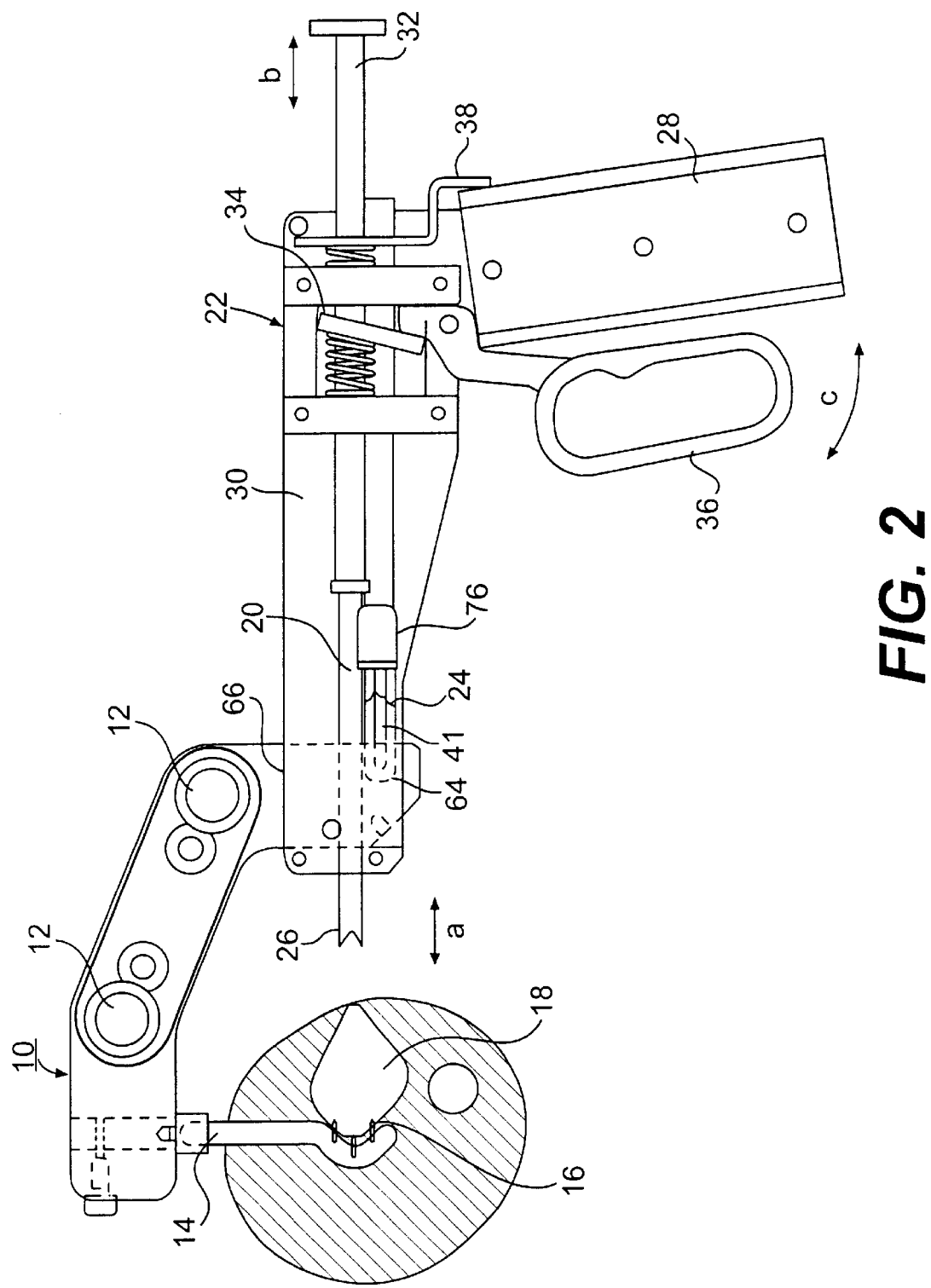
FIG. 2 is a view as in FIG. 1, with the fixation pin applicator shown in another operating position.
Figure 3:
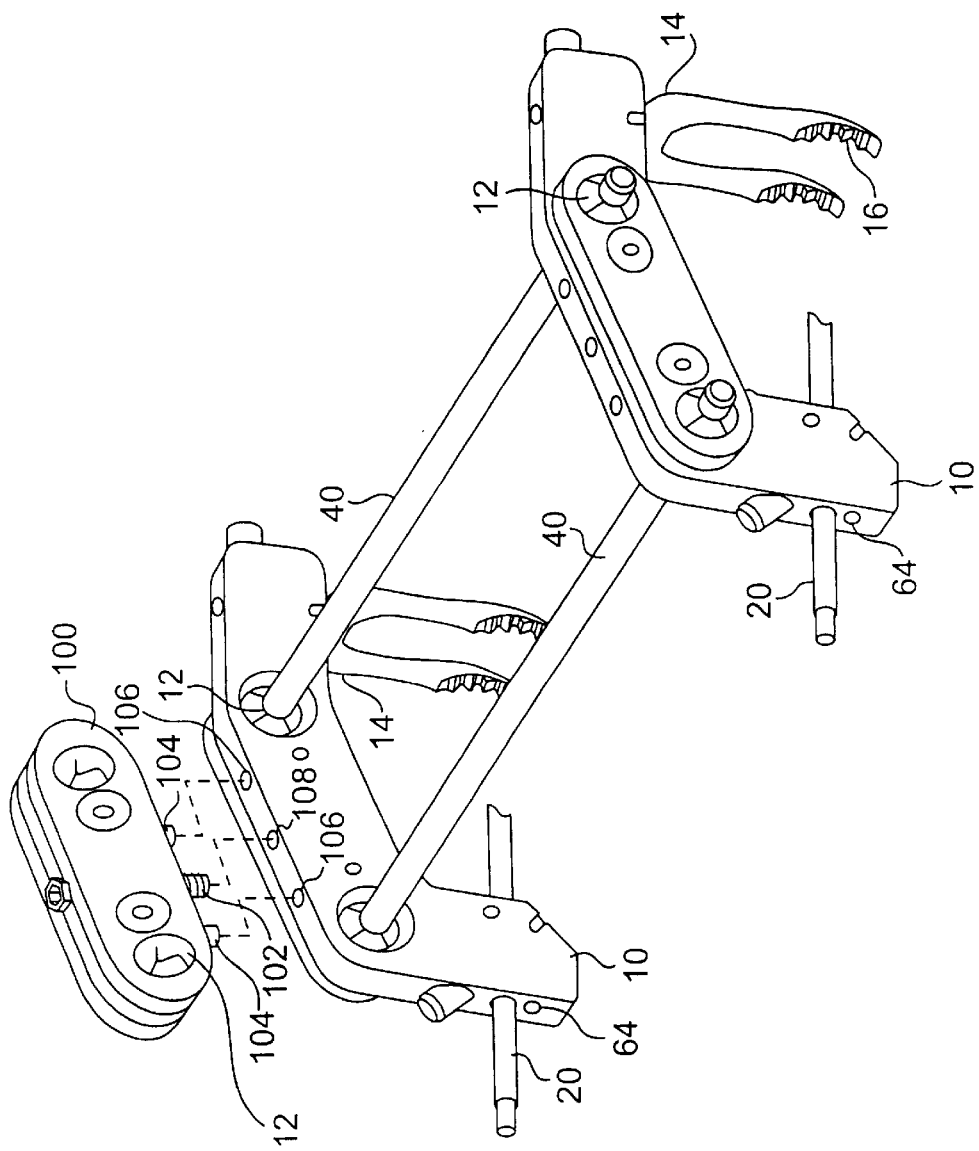
FIG. 3 is a perspective view showing two clamping jaws connected by two axial rods, according to an embodiment of the invention.
Figure 4:
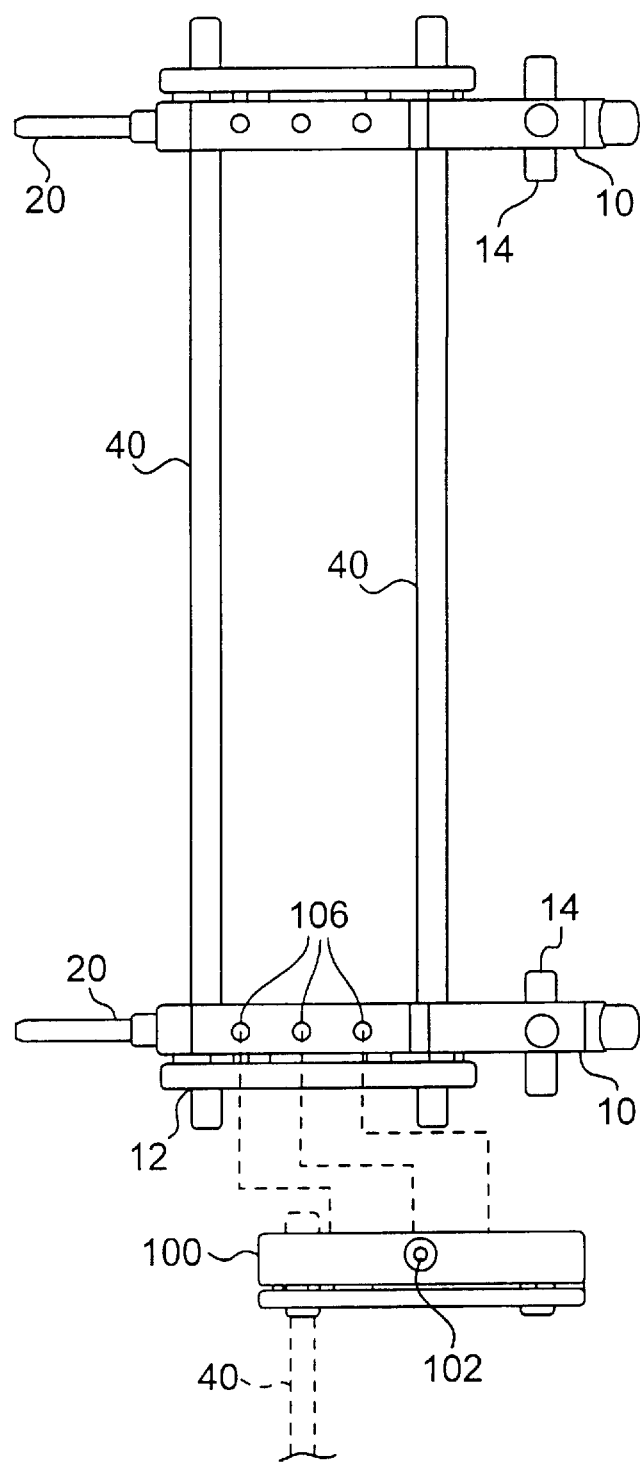
FIG. 4 is a top plan view showing the two clamping jaws and axial rods shown in FIG. 3.

The fixation device is formed from a plurality of clamping jaws. FIGS. 1 and 2 show one such clamping jaw 10, connected to a fixation pin applicator 22. As shown in FIGS. 3 and 4, clamping jaws 10 can be formed from straight sections bent at an angle with respect to one another, but can also be formed of sector rings or of curved segments. Clamping jaws 10 are connected by axial rods 40 that are axially displaceable in the clamping jaws and can be pivoted relative to the plane of clamping jaws 10. As a result, simple three-dimensional adjustment of clamping jaws 10 relative to one another is possible.

FIGS. 3 and 4 show one embodiment of an arrangement of two clamping jaws 10 and two axial rods 40. Axial rods 40 can pivot and can translate axially within clamping receptacles 12. Once clamping jaws 10 are positioned in a desired relative position, the axial rods 40 can be fixed to the clamping jaws 10 in a manner to be described later, so as to maintain the desired relative position between the two clamping jaws 10. In a preferred embodiment, the axial rods 40 are made of carbon fiber, however, other rigid materials could also be used.

When the desired position of the clamping jaws 10 is reached, the axial rods 40 are immobilized to maintain both axial and rotational position with respect to clamping jaws 10. Clamping jaws 10 are connected in stable fashion with one another, in a fixed relative position in space.

In a different embodiment according to the invention, more than two clamping jaws 10 can be connected by axial rods 40. This embodiment may require different sets of clamping receptacles 12 to connect respective pairs of clamping jaws with axial rods 40. For example, an add-on jaw 100 can be attached to the clamping jaw 10, as shown in FIG. 3. Add-on jaw 100 is similar to clamping jaw 10, but does not have provisions for pins 20 and 14. Two sets of axial rods 40 can be attached to the combination of clamping jaw 10, and add-on jaw 100, using the additional clamping receptacles 12 of the add-on jaw 100, so that more than two clamping jaws 10 can be connected together. As shown in FIGS. 3 and 4, add-on jaw 100 can be, for example, placed on top of clamping jaw 10 using guide pins 104 that fit in guide holes 106. Add-on jaw 100 can then be secured in place using fastener 102 fitting in fastener hole 108.

Figure 7:
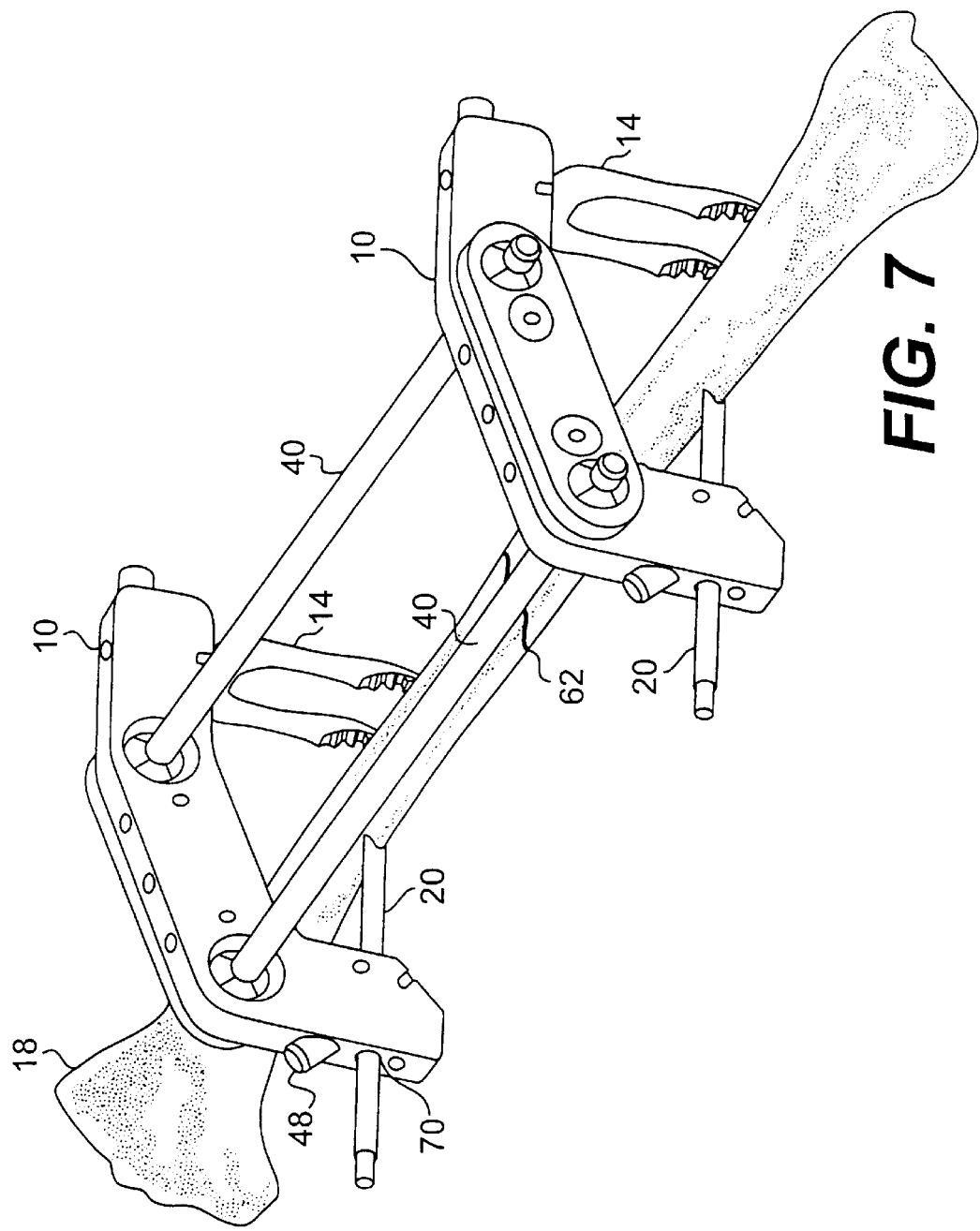
FIG. 7 is a perspective view illustrating the fixation device applied to a fractured bone.

As shown in FIG. 7, the clamping jaws 10 must be positioned and then maintained in a precise configuration so that a fractured bone 18 can be immobilized in a position suitable for healing. The invention can be used advantageously to treat, for example, a fractured tibia. However, other bones can also be treated by the invention. It is thus necessary that the clamping jaws 10 and axial rods 40 be easily fixed in a desired relative position, with at least one clamping jaw 10 on each side of fracture 62.

Figure 5:
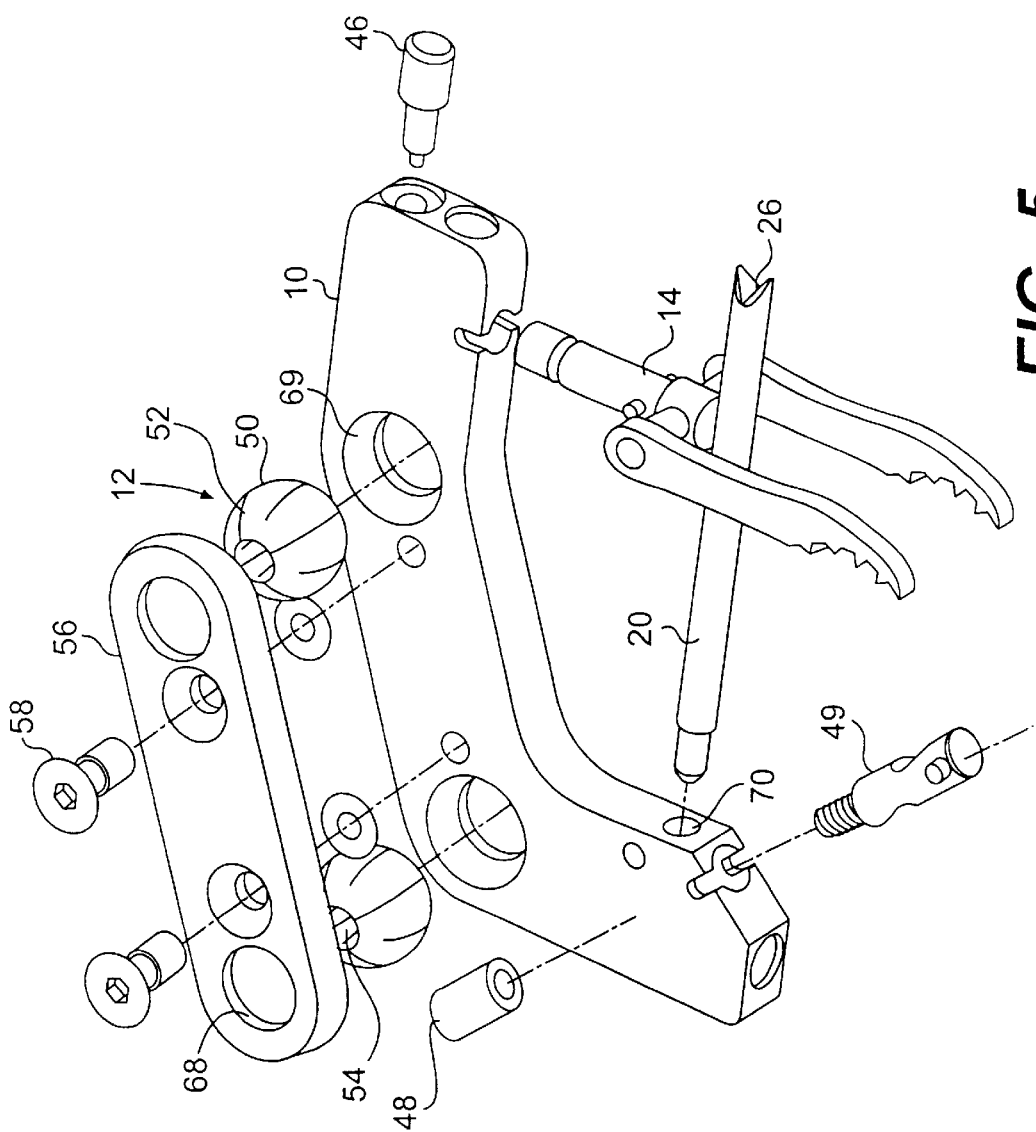
FIG. 5 is an exploded view showing a clamping jaw according to the invention.

Clamping jaws 10 have two clamping receptacles 12 to receive the axial rods, shown in detail in FIG. 5. Clamping receptacles 12 are equipped with clamping balls 50 that allow swiveling and axial translation of the rods, as described in greater detail in DE 41 13083A, incorporated herein by reference in its entirety. DE 94 02 291 U describes a more general system for swiveling and axially moving rods that are connected to sector rings, and is also incorporated herein by reference in its entirety. Clamping balls 50 have a passage 54 that extends diametrically across the ball, and is designed to receive axial rods 40. Clamping balls 50 also have slots 52 cut on their surface, along meridian lines. Slots 52 allow clamping ball 50 to contract radially by a small amount when squeezed, so that the diameter of passage 54 is reduced. The specific configuration of the slots 52 is not important, as long as they allow a reduction in diameter of passage 54 when the clamping ball 50 is squeezed.

Clamping jaw 10 is provided with a plate 56 used to squeeze clamping balls 50. Each one of clamping balls 50 is placed in a countersunk hole 69 of clamping jaw 10, and is held in place by plate 56, plate 56 is attached to clamping jaw 10 with fasteners 58, that can be, for example, screws. When screws 58 are loose, balls 50 are free to rotate in countersunk hole 69, and the diameter of passage 54 is at its greatest value. When screws 58 are tightened, plate 56 squeezes clamping balls 50 against countersunk hole 69, thus immobilizing them and minimizing the diameter of passage 54, which in turn immobilizes axial rods 40. The diameters of holes 69 and 68 are such that clamping balls 50 cannot pass through those holes.

In operation, axial rods 40 are inserted in passages 54 of the clamping balls 50 of a pair of clamping jaws 10, while screws 58 are loose. Once clamping jaws 10 are in the proper relative position, screws 58 are tightened, preventing further rotation of clamping balls 50, and translation of axial rods 40 within passages 54. The configuration of clamping jaws 10 and axial rods 40 cannot then be changed further.

A preferred embodiment according to the invention uses two axial rods 40 per pair of clamping jaws 10, with corresponding clamping receptacles 12. However, a different number of axial rods can be used, depending on the desired rigidity of the assembly. Plate 56 can also be made of multiple segments, or of a single segment, as shown in the drawings. Other suitable methods of squeezing clamping balls 50 could also be used, such as an arrangement of springs.

A retaining pin 14 can be inserted at one end of clamping jaw 10, perpendicularly to clamping jaw 10. This retaining pin 14, as shown in the embodiment illustrated here, can be designed as a so-called double-spoon pin. For this purpose, retaining pin 14 is curved at its free end so that it is spoon-shaped, and can have a plurality of ridges or points 16 that serve for increased grip with the cortex of a bone 18, as shown in FIG. 7.

Figure 6:
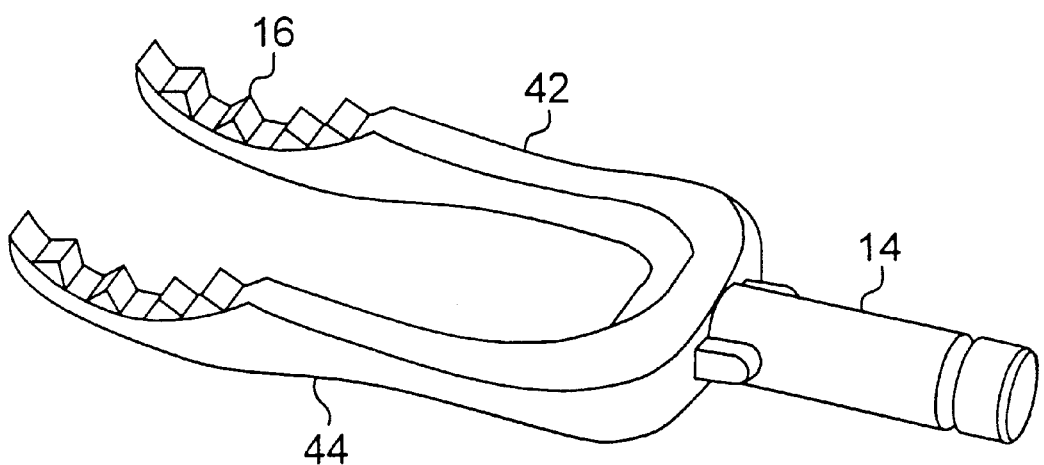
FIG. 6 is a perspective view showing one embodiment of the retaining pin according to the invention.

FIG. 6 shows one embodiment of a retaining pin 14 according to the invention. In this embodiment, retaining pin 14 has two prongs 42 and 44 that terminate in spoon shaped surfaces, with points 16 disposed on the concave side of the spoon shaped surfaces. As shown in FIG. 7, points 16 are designed to grip the surface of a bone 18, to facilitate retaining the clamping jaw 10 in position with respect to the bone 18.

Figure 8:
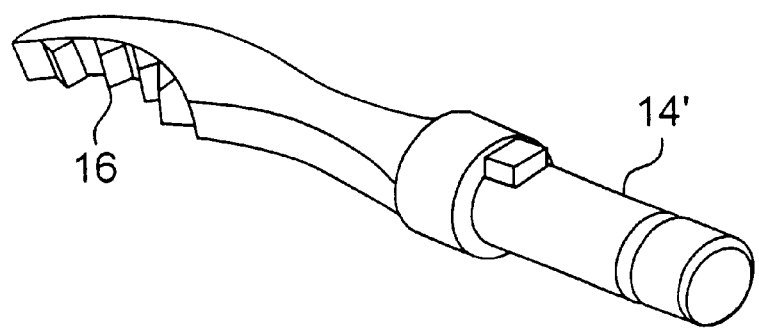
FIG. 8 is a perspective view showing a second embodiment of the retaining pin.

FIG. 8 shows a second embodiment of retaining pin 14', where only one prong is used. The single prong includes a spoon shaped surface with a concave side having points 16. Retaining pin 14 or 14' is securely attached to clamping jaw 10. This can be accomplished, for example, by using a set screw 46 shown in FIG. 5, or by any other suitable method, such as threading, spring loaded catches, or cotter pins.

At the opposite free end of clamping jaw 10, a fixation pin 20 is guided in an axially displaceable manner in the direction indicated by the double arrow "a", as shown in FIGS. 1, 2. For axial displaceability of fixation pin 20, in other words for positioning said pin in the cortex of bone 18, a fixation pin applicator 22 is connected securely but releasably to clamping jaw 10 by a latching mechanism 24, that will be described later.

Fixation pin 20 slides freely in hole 70 of clamping jaw 10, so that it can be positioned as desired abutting a portion of bone 18, as shown in FIG. 7. Once bone 18 is securely held between retaining pin 14 and fixation pin 20, the latter pin is secured in place on clamping jaw 10, to firmly retain clamping jaw 10 in position on bone 18. This is accomplished, for example, using a set nut 48 and bolt 49 shown in FIG. 5. For example, pin 20 can go through a hole in bolt 49, so it is held in place when nut 48 is tightened on bolt 49.

Fixation pin 20 can be positioned rapidly and simply at the desired location using fixation pin applicator 22. After fixation pin 20 has been positioned, in other words after points 26 of fixation pin 20 have engaged the cortex of bone 18 with a V-shaped portion of pin 20, fixation pin 20 is secured to the clamping jaw as described above. After fixation pin 20 has been secured to the clamping jaw, fixation pin applicator 22 can be released from clamping jaw 10, and the procedure can be repeated to position another clamping jaw 10 on bone 18.

Fixation pin applicator 22, described with reference to FIGS. 1, 2, 10 and 11, is designed in the shape of a pistol and has a fixed handle 28 and a housing 30 that resembles a pistol barrel. A piston or plunger 32 is located in housing 30, said plunger being axially displaceable in the direction b indicated by the double arrow, said plunger acting on the fixation pin 20 inserted into fixation pin applicator 22. Plunger 32 is displaceable by means of a transport plate 34. This transport plate is impacted upon by a movable handle part 36 as the movable handle part is pivoted in the direction c indicated by the double arrow. This kinematic arrangement is apparent from a comparison of FIG. 1 showing handle part 36 in its initial position and FIG. 2 showing the handle part in its pivoted position.

The operation of pin applicator 22 is conventional, and is designed to incrementally move plunger 32 towards passage 66. For example, piston 32 abuts fixation pin 20, which is loaded in hole 70 of clamping jaw 10, and is kept in place within housing 30 by guide ways 72 as it is pushed towards bone 18. A ratcheting mechanism, for example, can be used to allow motion of plunger 32 only in one direction, while fixation pin 20 is driven towards bone 18. A release lever 38 is also mounted on fixation pin applicator 22, said lever used to release piston 32 to pull it backwards, as shown in FIGS. 1 and 2.

A pin 41 that is part of latching mechanism 24 engages a catch 64 formed in clamping jaw 10. A bottom portion of clamping jaw 10 fits in an opening 66 of applicator 22, as shown in FIGS. 1, 2, 9 and 10. Once clamping jaw 10 is in position in opening 66, pin 41 engages catch 64, and keeps the two components attached. The fixation pin applicator can be released in simple fashion from clamping jaw 10 by actuating release lever 76, which pulls pin 41 out of catch 64.

Figure 10:
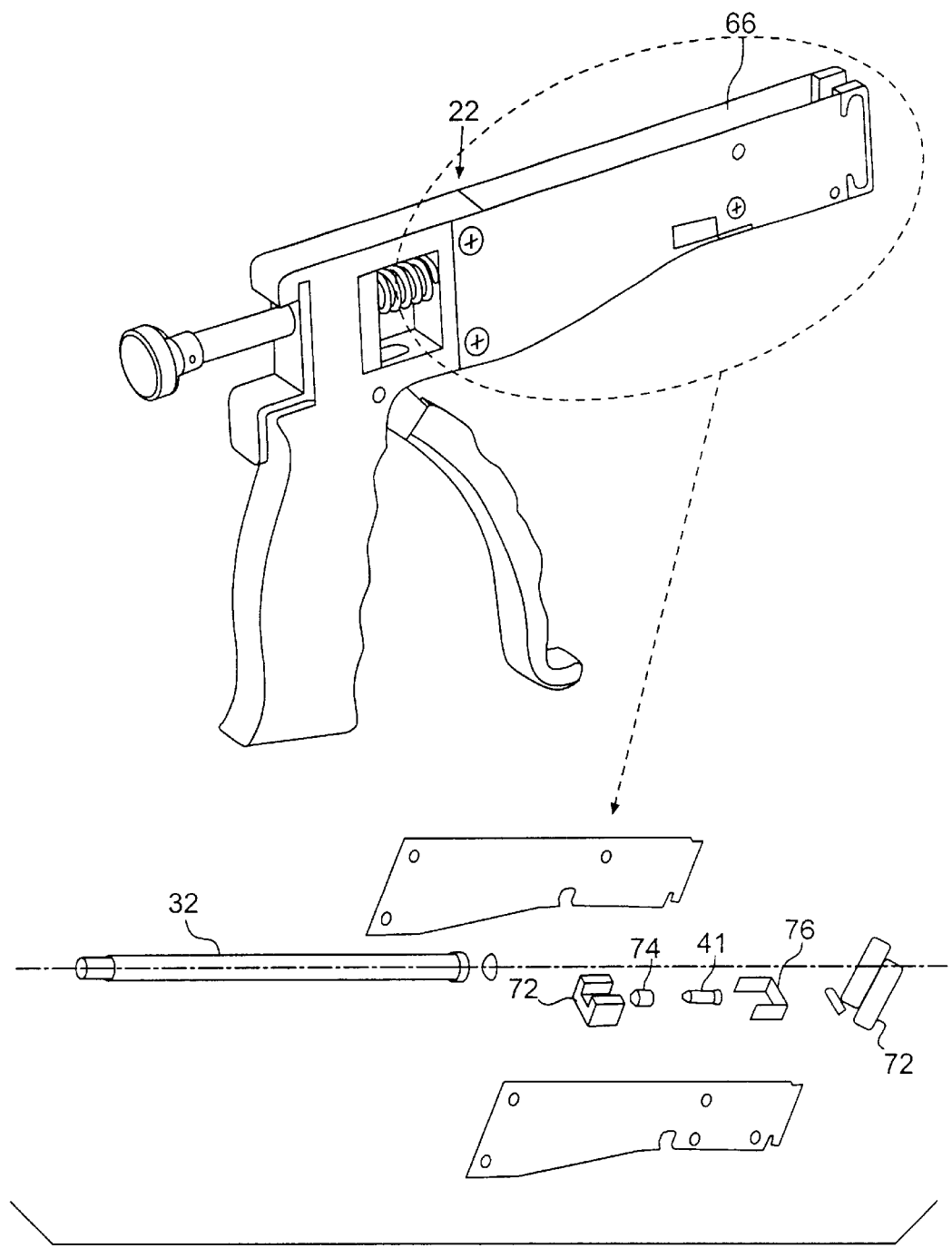
FIG. 10 is a diagram showing an exploded view of an embodiment of the fixation pin applicator.
Figure 11:
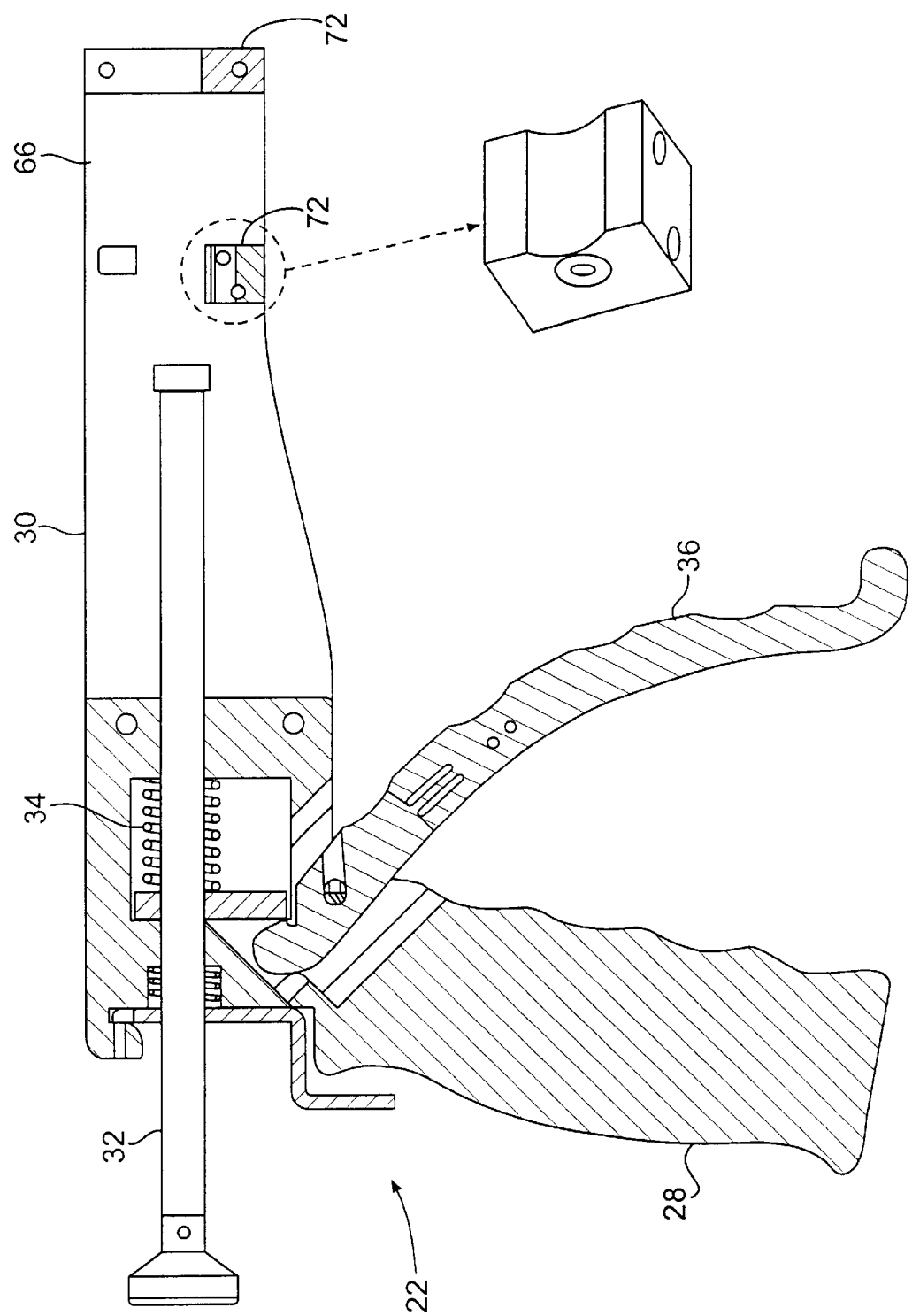
FIG. 11 is a cross sectional view of the fixation pin applicator shown in FIG. 10, also showing three views of the guide way.

Thus, as shown in FIGS. 9, 10 and 11, clamping jaw 10 is guided in opening 66 by guide ways 72. Locking pin 41 is pushed by spring 74 towards catch 64 of the clamping jaw 10, so that it automatically locks the clamping jaw in place once the jaw is positioned inside opening 66. Locking pin 41 is moved away from catch 64 using pin release handle 76, against the force of spring 74, so that clamping jaw 10 can be released from housing 30.

In a different embodiment, locking pin 41 could be replaced by a spring loaded sphere, pressed against catch 64 with sufficient force to retain clamping jaw 10 in place in pin applicator 22, while allowing separation of the two components if they are pulled apart. No actuator to release the two components is required for this embodiment.

The operation of the fixation device according to the invention is described in the following, with reference to FIGS. 1, 2 and 7. Clamping jaws 10 are initially fitted with the selected retaining pin 14. Then the fixation pin applicator is connected to the clamping jaw, with a selected fixation pin 20 being inserted. This clamping jaw, provided with pins 14 and 20, is placed over the portion of bone 18 where implantation is to occur and the appropriate perforations in the skin are marked. For each of the pins, or for each prong of the pins when applicable, a lengthwise incision approximately 8 to 10 mm long is made in the skin with a scalpel. The soft tissues are scraped away using a raspatory, and the bone is exposed down to the periosteum.

The selected retaining pins 14, attached to clamping jaw 10, are then introduced into the soft tissues between the bone and the raspatory, until retaining pins 14 gain a sufficient grip in the vicinity of the rear edge of the bone 18. Then fixation pin 20, also connected to clamping jaw 10, is introduced by means of fixation pin applicator 22 through the prepared skin incision in the area of the forward edge of the bone 18, until proper bone contact is achieved. The implants are finally fixed in place by multiple actuation of handle 36, which progressively pushes fixation pin 20 towards bone 18. A sufficient grip of clamping jaw 10 is obtained when the injured extremity can be lifted at the clamping jaw from the support without the pins tearing loose. In the same fashion, the fragment opposite the fracture is secured with one or more clamping jaws 10.

When dual pins are used, it is sufficient to connect the clamping jaws located proximally and distally with respect to the fracture by means of sufficiently long rods. The fracture is repositioned, for example, while being viewed on an x-ray image converter. As soon as the fragments are in close proximity and the axes of the fragments have been aligned, final fixation of the rods is performed.

It will be apparent to those skilled in the art that various modifications and variations can be made in the structure and the methodology of the present invention, without departing from the spirit or scope of the invention. Thus, it is intended that the present invention cover the modifications and variations of this invention provided they come within the scope of the appended claims and their equivalents.

What is claimed is:

1. A fixation device, comprising:
   a plurality of clamping jaws;
   at least one rod connecting the clamping jaws;
   a fixation pin adjustably mounted by and movable through each of the plurality of clamping jaws;
   a retaining pin mounted by each of the plurality of clamping jaws; and
   a fixation pin applicator releasably connectable with at least one of the clamping jaws to position the fixation pin relative to the retaining pin.

2. The fixation device according to claim 1, wherein the fixation pin applicator includes a fixed handle and a movable handle part.

3. The fixation device according to claim 2, further comprising a transport plate for moving a plunger against the force of a spring.

4. The fixation device according to claim 1, further comprising a latching mechanism for locking the fixation pin applicator to the clamping jaw.

5. The fixation device according to claim 4, wherein the fixation pin applicator comprises a release connected by a rod with the latching mechanism.

6. The fixation device according to claim 1, wherein the fixation pin is forked and has two prongs.

7. The fixation device according to claim 1, wherein the retaining pin is forked and has two prongs.

8. The fixation device according to claim 1, wherein the retaining pin has one prong.

9. The fixation device according to claim 1, wherein the fixation pin is directly contactable by the fixation pin applicator.

10. The fixation device according to claim 1, wherein the fixation pin has a longitudinal pin axis and is adjustably movable through one of the plurality of clamping jaws along the longitudinal pin axis.

11. The fixation device according to claim 1, wherein the rod is adjustable axially and angularly relative to the clamping jaws.

12. The fixation device according to claim 1, wherein at least one of the fixation pin and the retaining pin is mounted by each of the plurality of clamping jaws in a clampable fashion.

13. A fixation device, comprising:
    a plurality of clamping jaws;
    at least one rod connecting the clamping jaws;
    a fixation pin adjustably mounted by and movable through each of the plurality of clamping jaws;
    a retaining pin mounted by each of the plurality of clamping jaws and
    a fixation pin applicator having a latching mechanism, the latching mechanism releasably connectable with at least one of the clamping jaws to position the fixation pin relative to the retaining pin.

14. The fixation device according to claim 13, wherein the fixation pin applicator includes a fixed handle and a movable handle part.

15. The fixation device according to claim 14, further comprising a transport plate for moving a plunger against the force of a spring.

16. The fixation device according to claim 13, further comprising a latching mechanism for locking the fixation pin applicator to the clamping jaw.

17. The fixation device according to claim 16, wherein the fixation pin applicator comprises a release connected by a rod with the latching mechanism.

18. The fixation device according to claim 13, wherein the fixation pin is forked and has two prongs.

19. The fixation device according to claim 13, wherein the retaining pin is forked and has two prongs.

20. The fixation device according to claim 13, wherein the retaining pin has one prong.

21. The fixation device according to claim 13, wherein the fixation pin is directly contactable by the fixation pin applicator.

22. The fixation device according to claim 13, wherein the fixation pin has a longitudinal pin axis and is adjustably movable through one of the plurality of clamping jaws along the longitudinal pin axis.

23. The fixation device according to claim 13, wherein the rod is adjustable axially and angularly relative to the clamping jaws.

24. The fixation device according to claim 13, wherein at least one of the fixation pin and the retaining pin is mounted by each of the plurality of clamping jaws in a clampable fashion.

* * * * *